United States Patent
Steinbacher

(10) Patent No.: US 9,640,945 B2
(45) Date of Patent: May 2, 2017

(54) METHOD AND ARRANGEMENT FOR ACTUATING A WAVELENGTH-TUNABLE LASER DIODE IN A SPECTROMETER

(71) Applicant: Siemens Aktiengesellschaft, Munich (DE)

(72) Inventor: Franz Steinbacher, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/177,786

(22) Filed: Feb. 11, 2014

(65) Prior Publication Data

US 2014/0247843 A1    Sep. 4, 2014

(30) Foreign Application Priority Data

Feb. 13, 2013    (DE) .................. 10 2013 202 289

(51) Int. Cl.
| | |
|---|---|
| H01S 5/068 | (2006.01) |
| H01S 5/062 | (2006.01) |
| H01S 5/06 | (2006.01) |
| G01J 3/10 | (2006.01) |
| G01N 21/39 | (2006.01) |
| H01S 5/12 | (2006.01) |

(52) U.S. Cl.
CPC ............ *H01S 5/06808* (2013.01); *G01J 3/10* (2013.01); *G01N 21/39* (2013.01); *H01S 5/0622* (2013.01); *G01N 2021/399* (2013.01); *G01N 2201/069* (2013.01); *G01N 2201/0694* (2013.01); *H01S 5/0617* (2013.01); *H01S 5/12* (2013.01)

(58) Field of Classification Search
CPC ............... H01S 5/0617; H01S 5/06808; H01S 5/06812; H01S 5/0622
See application file for complete search history.

(56) References Cited

U.S. PATENT DOCUMENTS

| | | | |
|---|---|---|---|
| 4,782,243 A | 11/1988 | Rösl et al. | |
| 4,833,680 A | 5/1989 | Kaiser et al. | |
| 5,301,014 A | 4/1994 | Koch | |
| 5,414,280 A * | 5/1995 | Girmay ............... | H01S 5/06832 257/467 |
| 6,922,423 B2 * | 7/2005 | Thornton ................. | 372/38.07 |
| 7,668,216 B2 * | 2/2010 | Colbourne ............... | 372/38.07 |
| 2003/0099178 A1 * | 5/2003 | Sho ...................... | G11B 7/126 369/53.26 |
| 2006/0072867 A1 * | 4/2006 | Kawagishi ............... | 385/4 |
| 2007/0098415 A1 | 5/2007 | Lupo et al. | |

FOREIGN PATENT DOCUMENTS

| | | |
|---|---|---|
| CN | 1960087 | 5/2007 |
| DE | 3608930 | 9/1987 |
| DE | 4110095 | 10/1992 |
| DE | 102011079342 | 12/2012 |

* cited by examiner

*Primary Examiner* — Armando Rodriguez
*Assistant Examiner* — Sean Hagan
(74) *Attorney, Agent, or Firm* — Cozen O'Connor

(57) ABSTRACT

Method in which, in order to actuate a wavelength-tunable laser diode in a spectrometer, a power-time function is predetermined instead of a current-time function, wherein the laser diode is tuned periodically over a wavelength range in accordance with the power-time function. For this purpose, a current profile (i) with which the laser diode is actuated is determined from the power-time function and measured values of the voltage (u) present at the laser diode.

9 Claims, 2 Drawing Sheets

METHOD AND ARRANGEMENT FOR ACTUATING A WAVELENGTH-TUNABLE LASER DIODE IN A SPECTROMETER

BACKGROUND OF THE INVENTION

1. Field of the Invention

The invention relates to a method and arrangement for actuating a wavelength-tunable laser diode in a spectrometer, where a power-time function is predetermined, in accordance with which the laser diode is tuned periodically over a wavelength range by virtue of a current profile with which the laser diode is driven being determined from the power-time function and measured values obtained from the laser diode.

2. Description of the Related Art

A method and arrangement are known from DE 41 10 095 A1. In this document, the measured values are provided by a monitor diode that detects the radiation power of the laser diode. As a result, the optical power-current characteristic is linearized and thus the offset is reduced.

In laser absorption spectroscopy, the light of a wavelength-tunable laser diode is passed through a sample gas, and the concentration of a gas component of interest in the sample gas is determined based on the reduction in the light intensity caused by the absorption of the light at the point of a selected absorption line of the gas component, as explained in DE 102011079342 B3. In this case, the laser diode is actuated periodically corresponding to a predetermined current-time function, such as a current ramp, in order to sample the absorption line of the gas component in a wavelength-dependent manner. In addition to the current, the temperature of the laser diode to a strong degree also determines the intensity and wavelength of the light generated, for which reason the laser diode is mounted on a heat sink with temperature regulation. Owing to aging of the laser diode, the optical power is reduced and the wavelength of the light generated changes, with the result that further measures for wavelength stabilization are required. For this purpose, for example, the laser diode is actuated in each actuation period with two different successive current-time functions to sample an absorption line of a reference gas as well as the absorption line of the gas component to be measured. The temperature of the laser diode or of the heat sink is then regulated via the position of the absorption line of the reference gas such that the absorption line is always located at the same point, preferably the center of the current-time function in question. The wavelength spacing of the absorption line is known. As a result, the absorption line of the gas component to be measured is also always at the same point in the current-time function sampling it.

In the conventionally used types of laser diodes, i.e., a vertical cavity surface-emitting laser (VCSEL) and a distributed feedback (DFB) laser, the frequency-determining component is a Bragg reflector. This consists of a sequence of thin layers of alternating refractive index. Some of the incident light is reflected at each interface, where the reflected rays in a wavelength that corresponds to a quarter of the optical thickness of the layers are superimposed on one another constructively. In the region around this central wavelength, the reflection is very high and decreases severely for relatively large and relatively small wavelengths. The dimensions of the Bragg reflector can be varied by changing the temperature, where the wavelength increases as the temperature increases. The temperature of the Bragg reflector is determined by the power loss of the laser diode and the temperature of the heat sink. The power loss of the laser diode is in turn dependent on its current-voltage characteristic, which can be described by component parameters, such as threshold voltage and bulk resistance.

SUMMARY OF THE INVENTION

It is an object of the invention to enable a simplified wavelength stabilization without the use of a reference gas.

This and other objects and advantages are achieved in accordance with the invention by providing a method in which measured values are obtained from the voltage present at the laser diode.

The power supplied to the laser diode for the wavelength-dependent sampling of the absorption line of interest as a function of time is predetermined and is thus independent of the aging state of the laser diode. As a result, however, the power loss and the resultant heat development in the laser diode and therefore its temperature are also independent of the aging state of the laser diode. Although the efficiency of the laser diode and therefore the optical power decrease, the optical power is negligibly low in comparison with the supplied power and power loss, with the result that the supplied power and power loss can be equated.

In accordance with a first embodiment of the method in accordance with the invention, the current profile with which the laser diode is actuated directly is generated by a closed-loop control device depending on the system deviation between the power consumption (actual variable) of the laser diode and the predetermined power-time function (setpoint variable), where the voltage present at the laser diode and the current through the laser diode are continuously detected, such as measured, and the power consumption of the laser diode is determined continuously by multiplication of the measured current and voltage values.

It is also an object of the invention to provide an arrangement for implementing the method in accordance with the invention that correspondingly includes a device for continuously detecting the voltage present at the laser diode and the current through the laser diode, a device for continuously determining the power consumption of the laser diode by multiplication of the measured current and voltage values, and a closed-loop control device, which generates a current for actuating the laser diode depending on the system deviation between the power consumption of the laser diode as actual variable and a predetermined power-time function as setpoint variable. The closed-loop control device can contain, for example, a controller and a current source controlled thereby, to which the laser diode is connected. Here, a measurement of the current through the laser diode is not necessary because the controlled variable generated by the controller for the current source can be used instead of current measured values.

The first embodiment of the method in accordance with the invention is implemented with rapid sampling or a quick power-time function, preferably using hardware.

In a second embodiment of the method in accordance with the invention, a computation model is used that describes the current-voltage characteristic of the laser diode depending on predetermined component parameters of the laser diode. The voltage present at the laser diode and the current through the laser diode are determined regularly at different times to recalculate the component parameters each time. The current profile with which the laser diode is activated is determined via the computation model or the modeled current-voltage characteristic from the predetermined power-time function.

It is also an object to provide an arrangement for implementing the second embodiment of the method in accordance with the invention that correspondingly includes a device for regularly detecting the voltage present at the laser diode and the current through the laser diode at different times, and a computation device, in which a computation model is stored that describes the current-voltage characteristic of the laser diode depending on predetermined component parameters of the laser diode and that is configured to recalculate the component parameters based on the current and voltage values determined and to determine a current profile from a predetermined power-time function, and furthermore includes a controllable current source for actuating the laser diode in accordance with the determined current profile.

It is only necessary for the voltage at the laser diode to be measured because the current through the laser diode is calculated and is therefore known. In contrast to the first embodiment, in which the current and the voltage are measured continuously, in the second embodiment the current and voltage values are merely determined at different times. The number of times, i.e., the number of current and voltage value pairs required, is dependent on the number of component parameters (model parameters) of the current-voltage characteristic of the laser diode modeled by the computation model. The second embodiment of the method in accordance with the invention can therefore also be implemented with quick sampling or a quick power-time function using software.

The times at which the voltage present at the laser diode and the current through the laser diode are determined are preferably outside the time interval of the power-time function, where the laser diode is actuated at the different times with different currents, preferably as burst signals with different levels, and in the process the voltage across the laser diode is measured.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be explained below based on exemplary embodiments with reference to the figures in the drawing, in which.

DETAILED DESCRIPTION OF THE PREFERRED EMBODIMENTS

Figure 1:
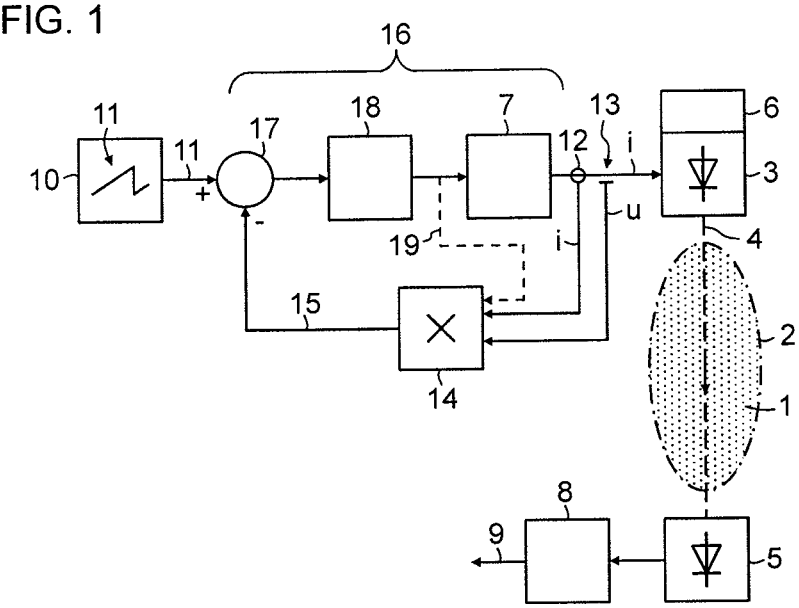
FIG. 1 shows a laser spectrometer with a first exemplary embodiment for an arrangement for actuating a wavelength-tunable laser diode.

FIG. 1 shows a laser spectrometer for measuring the concentration of at least one gas component of interest in a sample gas 1, which is contained in a measurement volume 2, such as a measurement cuvette or a process gas line. The spectrometer contains a laser diode 3, whose light 4 falls onto a detector 5 through the sample gas 1. The laser diode 3 is mounted on a temperature-regulated heat sink 6 and is actuated by a current source 7 with a periodically changing current (injection current) i. The intensity and wavelength of the light 4 generated are dependent on the current i and the operating temperature of the laser diode 3. Corresponding to the actuation of the laser diode 3 with the periodically changing current i, a selected absorption line of the gas component of interest is sampled periodically in a wavelength-dependent manner. The concentration of the gas component of interest is determined in an evaluation device 8 from the detected absorption at the point of the absorption line and is output as a measurement result 9.

A function generator 10 predetermines a preferably ramp-shaped or triangular power-time function 11, in accordance with which the laser diode 3 is intended to be tuned periodically over a wavelength range for sampling the absorption line. The current i flowing through the laser diode 3 and the voltage u present at the laser diode 3 are measured continuously using suitable measuring pickups 12, 13 and supplied to a multiplier 14 to continuously determine the present power consumption 15 of the laser diode 3. The power-time function 11 and the measured power consumption 15 are supplied as setpoint and actual variables, respectively, to a closed-loop control device 16, which contains a subtractor 17 for determining the system deviation between the setpoint variable and the actual variable, a controller 18, such as a proportional-integral-derivative (PID) controller, and the current source 7 and, depending on the system deviation, generates the current i for actuating the laser diode 3.

As indicated by the dashed line 19, the controlled variable generated by the controller 18 for the current source 7 can be used instead of the measured current i to determine the present power consumption 15 of the laser diode 3 together with the measured voltage u. The current i therefore does not need to be measured.

Figure 2:
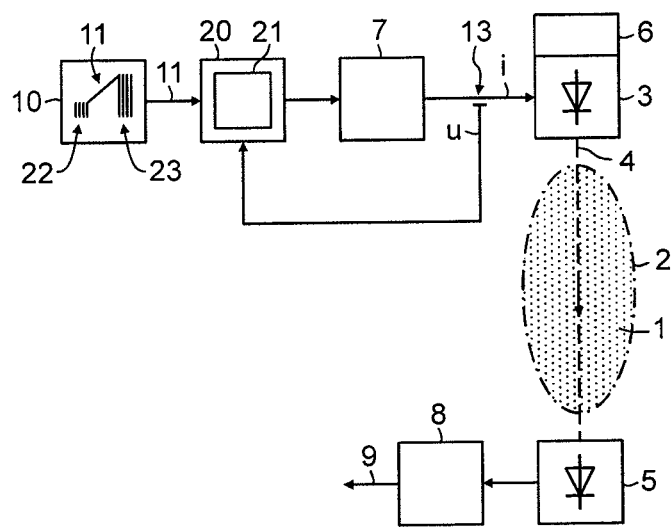
FIG. 2 shows the laser spectrometer with a second exemplary embodiment for the arrangement for actuating the laser diode.

FIG. 2 shows a laser spectrometer which is distinguished in terms of the actuation of the laser diode 3 from the exemplary embodiment shown in FIG. 1 in that, instead of the closed-loop control device 16, a computation model stored in a computation device 20 is provided, which computation model models the current-voltage characteristic 21 of the laser diode 3 depending on predetermined component parameters (model parameters) of the laser diode 3, recalculates the component parameters on the basis of present current and voltage values and determines the current profile i for actuating the laser diode 3 from the predetermined power-time function 11.

The current-voltage characteristic 21 can be described in simplified terms as follows:

$$u = U_S + R_B \cdot i,$$

where $U_S$ denotes the threshold voltage and $R_B$ denotes the bulk resistance of the laser diode 3. For the power $P_L$ supplied to the laser diode 3, the following then applies:

$$P_L = (U_S + R_B \cdot i) \cdot i$$

The optical power is negligibly low in comparison with $P_L$. As a result, $P_L$ also corresponds to the power loss of the laser diode 3.

The two component parameters $U_S$ and $R_B$ can be determined based on two measurements of the current $I_1$, $I_2$ and the voltage $U_1$, $U_2$:

$$U_1 = U_S + R_B \cdot I_1$$

$$U_2 = U_S + R_B \cdot I_2$$

Using the component parameters $U_S$ and $R_B$ thus determined and updated regularly, such as every n-th period, the current i for actuating the laser diode 3 is determined as follows:

$$i = \frac{1}{2R_B} \cdot \left(-U_S + \sqrt{U_S^2 + 4R_B \cdot P_L}\right).$$

In order to measure the current $I_1$, $I_2$ and the voltage $U_1$, $U_2$, the function generator 10 can generate two burst signals 22, 23 of different levels at different times, such as prior to and after every n-th power-time function 11.

Figure 3:
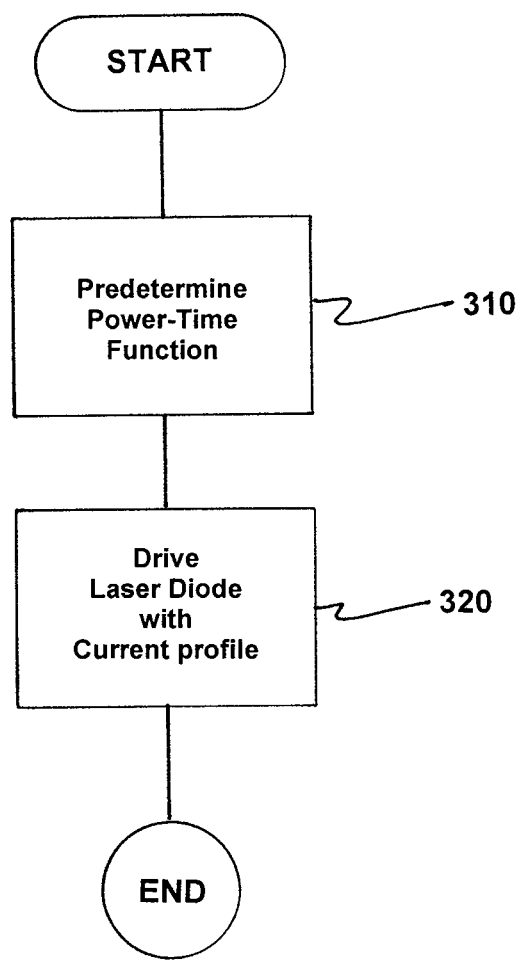
FIG. 3 is a flowchart of the method in accordance with the invention.

FIG. 3 is a flowchart of a method for actuating a wavelength-tunable laser diode (3) in a spectrometer. The method comprises predetermining a power-time function (11), as indicated in step 310. Next, the driving the laser diode (3) is driven with a current profile (i) determined from the predetermined power-time function (11) and measured values obtained from the laser diode (3) to periodically tune the laser diode (3) over a wavelength range in accordance with the predetermined power-time function (11), as indicated in step 320. In accordance with the method of the invention, the measured values are obtained from a voltage (u) present at the laser diode (3).

While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for actuating a wavelength-tunable laser diode in a spectrometer, comprising:
    predetermining a setpoint variable indicating an electrical power value to be supplied to the wavelength-tunable laser diode as a variable function of time;
    measuring a voltage present at the laser diode; and
    driving the laser diode continuously and periodically with a current profile which is determined from (i) the predetermined setpoint variable indicating the electrical value to be supplied to the wavelength-tunable laser diode as the variable function of time and (ii) the measured voltage to periodically tune the laser diode over a wavelength range in accordance with the setpoint variable indicating the electrical value to be supplied to the wavelength-tunable laser diode as the variable function of time.

2. The method as claimed in claim 1, wherein the current profile is generated by a closed-loop control device depending on a system deviation between a power consumption of the laser diode as an actual variable and the setpoint variable of electrical power supplied to the wavelength-tunable laser diode over time; and wherein the voltage present at the laser diode and the current through the laser diode are continuously detected and the power consumption of the laser diode is continuously determined by multiplication of the measured current and voltage values.

3. The method as claimed in claim 1, wherein a computation model is selected which describes a current-voltage characteristic of the laser diode depending on predetermined component parameters of the laser diode; and wherein the voltage present at the laser diode and the current through the laser diode are regularly determined at different times, and component parameters are recalculated based on determined current and voltage values, said component parameters comprising a threshold voltage and a bulk resistance of the laser diode; and wherein the current profile with which the laser diode is driven is determined from the power-time function via the computation model.

4. The method as claimed in claim 3, wherein times at which the voltage present at the laser diode and the current through the laser diode are determined reside outside a time interval of the power-time function; and wherein the laser diode is supplied with different currents at different times and, during this process, a voltage across the laser diode is measured.

5. The method as claimed in claim 4, wherein the different currents are generated as burst signals having different levels.

6. An arrangement for actuating a wavelength-tunable laser diode, comprising:
    at least one measuring pickup for continuously detecting a voltage present at the laser diode and a current through the laser diode;
    a multiplier for continuously determining a power consumption of the laser diode by multiplication of a measured current and voltage values; and
    a closed-loop control device, which generates the current, for driving the laser diode continuously and periodically with a current profile which is determined from (i) the detected voltage present at the laser diode and (ii) a predetermined setpoint variable indicating an electrical value to be supplied to the wavelength-tunable laser diode as a variable function of time.

7. The arrangement as claimed in claim 6, wherein the closed-loop control device includes a controller and a current source controlled by the controller.

8. The arrangement as claimed in claim 6, further comprising:
    a computation device have a stored computation model describing a current-voltage characteristic of the laser diode depending on predetermined component parameters of the laser diode, the component parameters comprising a threshold voltage and a bulk resistance of the laser diode, and the computation device being configured to recalculate the component parameters based on the measured current and voltage values and to determine a current profile from a predetermined power-time function; and
    a controllable current source for actuating the laser diode in accordance with the determined current profile;
    wherein the at least one measuring pickup regularly detects the voltage present at the laser diode and the current through the laser diode at different times.

9. The arrangement as claimed in claim 6, wherein the current profile is generated by the closed-loop control device depending on a system deviation between a power consumption of the laser diode as an actual variable and the setpoint variable of electrical power supplied to the wavelength-tunable laser diode over time; and wherein the voltage present at the laser diode and the current through the laser diode are continuously detected and the power consumption of the laser diode is continuously determined by multiplication of measured current and voltage values.

* * * * *